US008277403B2

(12) United States Patent
Ceriani et al.

(10) Patent No.: US 8,277,403 B2
(45) Date of Patent: Oct. 2, 2012

(54) SUPPORT ASSEMBLY FOR AN ORTHOPEDIC BRACE HAVING A LENGTH-ADJUSTING MECHANISM

(75) Inventors: Dylann D. Ceriani, San Diego, CA (US); James D. Burke, Encinitas, CA (US); Paul Oddou, Oceanside, CA (US)

(73) Assignee: Breg, Inc., Carlsbad, CA (US)

( * ) Notice: Subject to any disclaimer, the term of this patent is extended or adjusted under 35 U.S.C. 154(b) by 785 days.

(21) Appl. No.: 11/039,056

(22) Filed: Jan. 12, 2005

(65) Prior Publication Data

US 2006/0155229 A1   Jul. 13, 2006

(51) Int. Cl.
*A61F 5/37* (2006.01)
*A61F 13/00* (2006.01)
*A61F 5/00* (2006.01)
*A61F 13/06* (2006.01)

(52) U.S. Cl. .......... 602/26; 128/846; 128/878; 128/881; 128/882; 602/5; 602/12; 602/16; 602/20; 602/23; 602/62

(58) Field of Classification Search .......... 128/878–879, 128/882; 602/5, 16, 26, 62; 292/292, 259 R, 292/339, 241, 218, 300, 403; D24/192; 410/151
See application file for complete search history.

(56) References Cited

U.S. PATENT DOCUMENTS

| 401,933 | A |   | 4/1889  | De Camp |   |
|---------|---|---|---------|---------|---|
| 552,143 | A |   | 12/1895 | Rankin  |   |
| 649,237 | A | * | 5/1900  | Dyson   | 602/16 |
| 2,853,999 | A | * | 9/1958 | Risser  | 602/39 |
| 3,439,672 | A |   | 4/1969  | Fisher  | 128/88 |
| 3,805,773 | A |   | 4/1974  | Sichau  | 128/80 E |
| 4,481,941 | A |   | 11/1984 | Rolfes  | 128/87 R |
| 4,489,718 | A |   | 12/1984 | Martin  | 128/80 C |
| 4,531,515 | A |   | 7/1985  | Rolfes  | 128/87 R |
| 4,620,532 | A |   | 11/1986 | Houswerth | 128/80 C |
| 4,655,201 | A |   | 4/1987  | Pirmantgen | 128/80 C |
| 4,776,326 | A |   | 10/1988 | Young et al. | 128/80 F |
| 4,817,588 | A |   | 4/1989  | Bledsoe | 128/80 C |
| 4,982,732 | A | * | 1/1991  | Morris  | 602/16 |
| 5,000,169 | A |   | 3/1991  | Swicegood et al. | 128/80 C |
| 5,018,514 | A |   | 5/1991  | Grood et al. | 128/80 C |
| 5,052,379 | A |   | 10/1991 | Airy et al. | 128/80 C |
| 5,062,858 | A |   | 11/1991 | Broeck et al. | 623/43 |
| 5,138,911 | A |   | 8/1992  | Lan     | 81/177.2 |
| 5,292,303 | A |   | 3/1994  | Bastyr et al. | 602/16 |
| 5,409,449 | A |   | 4/1995  | Nebolon | 602/16 |
| 5,425,700 | A | * | 6/1995  | Aaserude et al. | 602/16 |
| 5,443,444 | A |   | 8/1995  | Pruyssers | 602/26 |
| 5,460,599 | A |   | 10/1995 | Davis et al. | 602/26 |
| 5,653,680 | A |   | 8/1997  | Cruz    | 602/21 |
| 5,658,241 | A |   | 8/1997  | Deharde et al. | 602/5 |
| 5,658,243 | A |   | 8/1997  | Miller et al. | 602/26 |
| 5,672,152 | A |   | 9/1997  | Mason et al. | 602/26 |
| 5,814,000 | A |   | 9/1998  | Kilbey  | 602/16 |
| 5,817,040 | A |   | 10/1998 | Hess et al. | 602/26 |
| 5,827,208 | A |   | 10/1998 | Mason et al. | 602/16 |
| 5,921,946 | A |   | 7/1999  | Tillinghast et al. | 602/16 |
| 6,347,817 | B1 | * | 2/2002 | Chou   | 292/259 R |
| 6,383,156 | B1 | * | 5/2002 | Enzerink et al. | 602/16 |
| 7,022,094 | B2 | * | 4/2006 | Buckman et al. | 602/23 |
| 7,083,583 | B2 | * | 8/2006 | Opahle et al. | 602/16 |
| 2002/0072695 | A1 | * | 6/2002 | Doty et al. | 602/5 |
| 2002/0183672 | A1 | * | 12/2002 | Enzerink et al. | 602/16 |
| 2006/0155230 | A1 | * | 7/2006 | Mason et al. | 602/16 |

* cited by examiner

*Primary Examiner* — Patricia Bianco
*Assistant Examiner* — Brandon L Jackson
(74) *Attorney, Agent, or Firm* — Rodney F. Brown

(57) ABSTRACT

An adjustable support assembly for an orthopedic brace has a support arm, a housing and a locking mechanism. The housing includes a travel track which slidably receives the support arm. The locking mechanism includes a lock lever which selectively applies a sufficient force to the support arm to prevent slidable displacement of the support arm in the travel track.

16 Claims, 10 Drawing Sheets

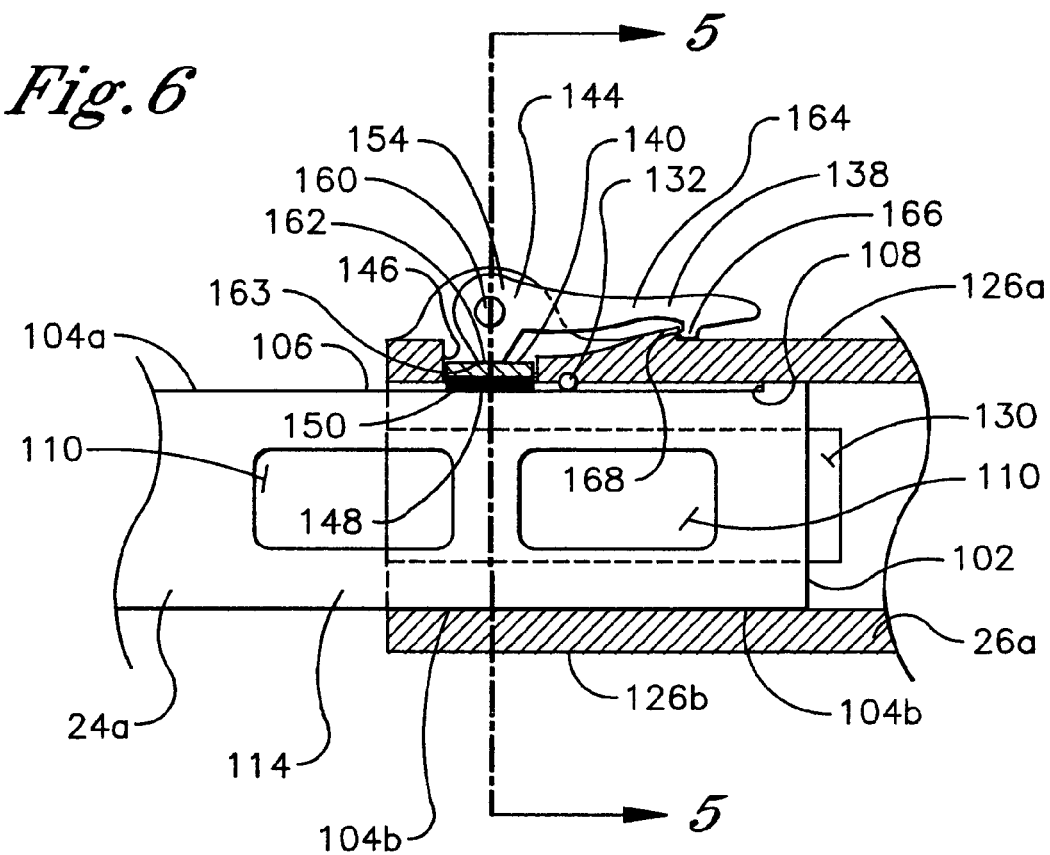
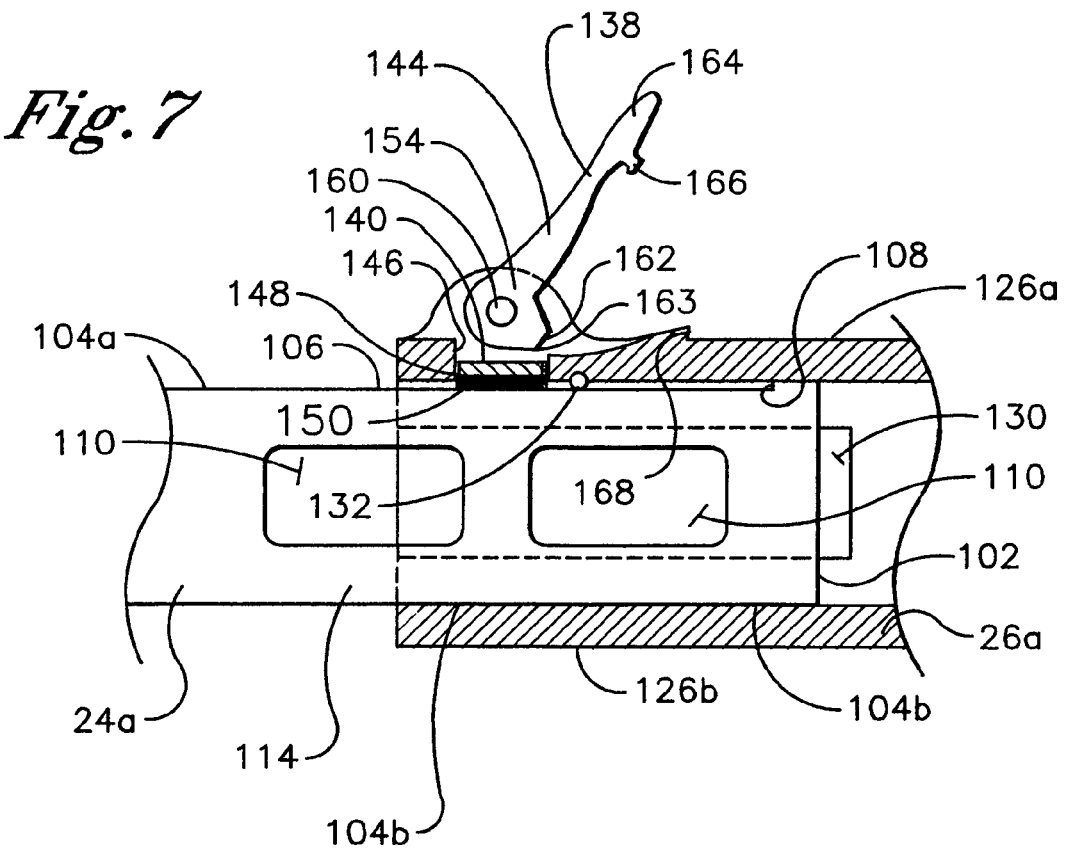

SUPPORT ASSEMBLY FOR AN ORTHOPEDIC BRACE HAVING A LENGTH-ADJUSTING MECHANISM

TECHNICAL FIELD

The present invention relates generally to orthopedic braces, and more particularly to a support assembly for an orthopedic brace, having a length-adjusting mechanism and a locking mechanism for adjusting the length of the support assembly to a selected length and releasably locking the support assembly at the selected length.

BACKGROUND OF THE INVENTION

Orthopedic braces are worn on the body of a user either to support a healthy skeletal joint that is at risk of injury or to stabilize a skeletal joint that has been destabilized by an injury or other condition. Orthopedic braces generally include rigid structural components to support or stabilize the skeletal joint. Frequently, although not necessarily, the rigid structural components are dynamically linked together by one or more hinges enabling controlled pivotal movement of the skeletal joint during user activity or rehabilitative therapy. The orthopedic brace is positioned on the body such that the hinges traverse the skeletal joint, while the rigid components are secured to the body above and below the skeletal joint.

In some instances, it is desirable to enable the user or provider of the orthopedic brace to adjust the dimensions of the rigid components. This feature allows the manufacture of a single adjustable orthopedic brace which is capable of being fitted to a number of different sized users. This feature also allows the manufacture of an orthopedic brace which is capable of being adapted over time to the evolving therapeutic treatment requirements of a single user. For example, a user often requires an orthopedic brace providing a high degree of immobility and/or stability immediately following surgery to a skeletal joint such as the knee. Generally, an orthopedic brace, which extends virtually the entire length of the limb on either side of the afflicted skeletal joint, i.e., the upper and lower leg in the case of the knee, provides the highest degree of immobility and/or stability. Therefore, post-operative knee braces typically have relatively long rigid support members for mounting on the leg above and below the knee.

As rehabilitation of the repaired skeletal joint progresses following surgery, an orthopedic brace providing an increased degree of mobility is usually desirable while possibly tolerating a lesser degree of stability. The mobility of an orthopedic brace can often be increased simply by shortening the length of the rigid support members. Thus, an orthopedic brace with rigid support members having an adjustable length are highly desirable for post-operative application. The adjustable orthopedic brace obviates the need and expense of periodically replacing the initial orthopedic brace with gradually less restrictive orthopedic braces as rehabilitation progresses.

Accordingly, it is an object of the present invention to provide an orthopedic brace with rigid supports which have adjustable dimensions. In particular, it is an object of the present invention to provide an orthopedic brace with rigid longitudinal supports which have adjustable lengths. It is further an object of the present invention to provide such an adjustable orthopedic brace, wherein adjustment of the rigid supports to alternate dimensions is relatively simple. It is another object of the present invention to provide such an adjustable orthopedic brace, wherein the rigid supports reliably maintain their alternate adjusted dimensions during normal use of the brace until it is desired to readjust the dimensions. These objects and others are accomplished in accordance with the invention described hereafter.

SUMMARY OF THE INVENTION

The present invention is characterized as an adjustable support assembly for an orthopedic brace comprising a support arm, a housing and a locking mechanism. The housing includes a travel track which slidably receives the support arm. The locking mechanism includes a lock lever selectively transitionable between a closed position and an open position. When the lock lever is in the closed position, the lock lever applies a sufficient degree of a pressing force to the support arm to prevent slidable displacement of the support arm in the travel track. The lock lever preferably applies the pressing force to the support arm in a force direction essentially perpendicular to a travel direction of the support arm in the travel track. When the lock lever is in the open position, the lock lever withdraws a sufficient degree of the pressing force from the support arm to enable slidable displacement of the support arm in the travel track.

The lock lever preferably has a head rotationally mounted on the housing and the locking mechanism further includes a lock chamber formed in the housing to receive the head. The lock chamber has an internal opening which enables access to the support arm in the travel track from the lock chamber. In accordance with a specific embodiment of the present characterization, the head engages the support arm through the internal opening to apply the pressing force to the support arm when the lock lever is in the closed position. In accordance with an alternate specific embodiment of the present characterization, the locking mechanism includes a friction plate positioned in the internal opening. The friction plate engages the head and the support arm when the lock lever is in the closed position and the lock lever applies the pressing force to the support arm via the friction plate. The friction plate preferably has a first layer engageable with the head and a second layer engageable with the support arm. The first layer is formed from a relatively non-compressible material and the second layer is formed from a relatively elastically compressible material.

Another characterization of the present invention is an orthopedic brace comprising a first support assembly having a first support arm, a first housing and a first locking mechanism. The first housing includes a first travel track which slidably receives the first support arm. The first locking mechanism includes a first lock lever selectively transitionable between a first closed position and a first open position. When the first lock lever is in the first closed position, the first lock lever applies a sufficient degree of a first pressing force to the first support arm to prevent slidable displacement of the first support arm in the first travel track. When the first lock lever is in the first open position, the first lock lever withdraws a sufficient degree of the first pressing force from the first support arm to enable slidable displacement of the first support arm in the first travel track.

The orthopedic brace further comprises a second support assembly having a second support arm, a second housing and a second locking mechanism. The second housing includes a second travel track which slidably receives the second support arm. The second locking mechanism includes a second lock lever selectively transitionable between a second closed position and a second open position. When the second lock lever is in the second closed position, the second lock lever applies a sufficient degree of a second pressing force to the second support arm to prevent slidable displacement of the second support arm in the second travel track. When the second lock lever is in the second open position, the second lock lever withdraws a sufficient degree of the second pressing force from the second support arm to enable slidable displacement of the second support arm in the second travel track.

The orthopedic brace still further comprises a joint connecting the first support assembly to the second support assembly. The joint is preferably either a static joint or a rotational hinge.

Another characterization of the present invention is an adjustable support assembly for an orthopedic brace comprising a support arm, a housing and a travel limit. The support arm has an edge with an indentation formed therein to define a step on the edge at a terminus of the indentation. The housing includes a travel track slidably receiving the support arm. The travel limit is positioned in the travel track and is preferably a post mounted in the housing. The indentation clears the travel limit when the support arm is slidably displaced in a travel direction within the travel track, but the travel limit engages the step when the support arm is slidably displaced in the travel direction within the travel track to a position where the step is aligned with the travel limit. As such, the travel limit prevents further slidable displacement of the support arm in the travel direction within the travel track.

In accordance with a specific alternate embodiment of the present characterization, the adjustable support assembly further comprises a locking mechanism including a lock lever selectively transitionable between a closed position and an open position. When the lock lever is in the closed position, the lock lever applies a sufficient degree of a pressing force to the indentation to prevent slidable displacement of the support arm in the travel track. When the lock lever is in the open position, the lock lever withdraws a sufficient degree of the pressing force from the indentation to enable slidable displacement of the support arm in the travel track.

Another characterization of the present invention is a method for adjusting the length of a support assembly for an orthopedic brace. The method provides a support assembly having a support arm and a housing with a travel track. The travel track is sized to receive the support arm therein and the support assembly has a plurality of selected lengths, each selected length corresponding to a different position of the support arm in the travel track. The support arm is positioned in the travel track at a first position such that the support assembly has a first selected length. The support arm is then slidably displaced in a travel direction in the travel track to a second position such that the support assembly has a second selected length different than the first selected length. The support arm is locked in the second position to maintain the support assembly at the second selected length by applying a pressing force in a force direction to the support arm sufficient to prevent slidable displacement of the support arm in the travel track.

The present invention will be further understood from the drawings and the following detailed description.

BRIEF DESCRIPTION OF THE DRAWINGS

FIG. 6 is a detailed cross-sectional view of the locking mechanism in the support assembly of FIG. 4, which is taken along line 6-6 (shown in FIG. 5), wherein the locking mechanism is in the closed position.

FIG. 7 is a detailed cross-sectional view of the locking mechanism in the support assembly of FIG. 4, wherein the locking mechanism is in an open position.

DESCRIPTION OF PREFERRED EMBODIMENTS

Figure 1:
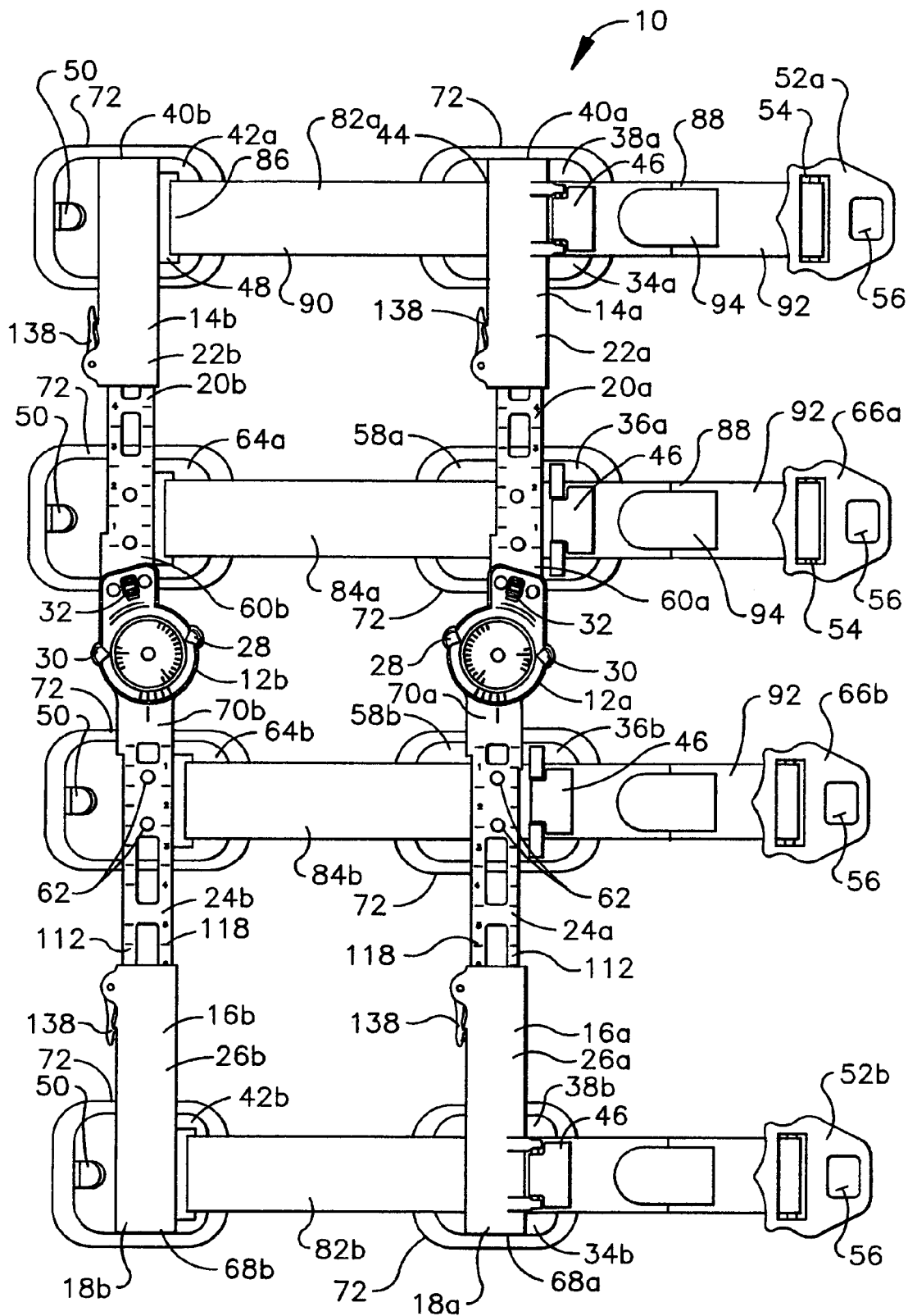
FIG. 1 is a plan view of an orthopedic brace including a plurality of support assemblies having the length-adjusting and locking mechanisms of the present invention.

Referring initially to FIG. 1, an orthopedic brace is shown and generally designated 10. There are a number of relative terms defined below which are used in the following description to distinguish various elements of the orthopedic brace 10 from one another, but which are not to be construed as limiting the scope of the invention. The relative terms "medial" and "lateral" characterize certain elements of the orthopedic brace 10 and, in particular, describe the relative proximity of the given element to the central longitudinal axis of the body of the user when the brace 10 is mounted thereon. A "medial" element is closer to the central longitudinal axis of the body, while a "lateral" element is further from the central longitudinal axis of the body.

The terms "proximal" and "distal" characterize certain elements of the brace 10, which are aligned with the longitudinal axis of the brace 10. The terms describe the relative proximity of the given element to the central joint of the brace 10. A "proximal" element is closer to the central joint of the brace 10, while a "distal" element is further from the central joint of the brace 10. The terms "upper" and "lower" likewise characterize certain elements of the brace 10, which are aligned with the longitudinal axis of the brace 10. However, the terms describe the position of the given element as being either above or below a horizontal plane running through the central joint of the brace 10. In particular, an "upper" element is above the horizontal plane running through the central joint of the brace 10, while a "lower" element is below the horizontal plane running through the central joint of the brace 10.

The relative terms "posterior" and "anterior" characterize certain elements of the orthopedic brace 10 and, in particular, describe the orientation of the given element relative to the central longitudinal axis of the body of the user when the brace 10 is mounted thereon. A "posterior" element is positioned behind the central longitudinal axis of the body in correspondence with the posterior of the body, while an "anterior" element is positioned in front of the central longitudinal axis of the body in correspondence with the posterior of the body.

The orthopedic brace 10 comprises a lateral central joint 12a, a lateral upper support assembly 14a and a lateral lower support assembly 16a, which in combination define a lateral longitudinal brace assembly 18a. The lateral upper support assembly 14a includes a lateral upper support arm 20a and a lateral upper housing 22a. The lateral lower support assembly 16a similarly includes a lateral lower support arm 24a and a lateral lower housing 26a, having a construction substantially similar to the lateral upper support arm 20a and lateral upper housing 22a, respectively. The lateral central joint 12a connects the lateral upper support assembly 14a with the lower support assembly 16a such that the lateral upper and lower support assemblies 14a, 16a extend radially from the lateral central joint 12a. Details of the lateral upper and lower support assemblies 14a, 16a are described below in association with the length-adjusting and locking mechanisms of the present invention.

The lateral central joint 12a is preferably a dynamic joint, which dynamically connects the lateral upper and lower support assemblies 14a, 16a, and is more preferably a rotational hinge, which rotationally connects the lateral upper and lower support assemblies 14a, 16a. The lateral central joint 12a is most preferably a releasably locking rotational hinge with adjustable rotation limits as shown herein. The releasably locking rotational hinge includes a flexion rotation stop 28, an extension rotation stop 30 and a lock actuator 32. Further details of the structure and operation of the releasably locking rotational hinge are disclosed in commonly-owned U.S. Pat. No. 7,235,059 issued on Jun. 26, 2007 entitled "Releasably Locking Hinge for an Orthopedic Brace Having Adjustable Rotation Limits" filed as U.S. patent application Ser. No. 11/039,448 on Jan. 12, 2005, which is incorporated herein by reference.

Notwithstanding the above, it is understood that the lateral central joint 12a is not limited to any one specific construction or type of joint. Thus, most conventional hinges for orthopedic braces, which enable rotation of the lateral upper longitudinal support assembly 14a and/or the lateral lower longitudinal support assembly 16a about the hinge, are alternatively employed as the lateral central joint 12a of the orthopedic brace 10. Exemplary prior art hinges are disclosed in U.S. Pat. Nos. 401,933; 4,481,941; 5,672,152; and 5,827,208. In yet another alternative, not shown, the lateral central joint 12a is a static joint which does not enable rotation of the lateral upper longitudinal support assembly 14a and/or the lateral lower longitudinal support assembly 16a about the joint. In accordance with this embodiment, the positions of the lateral upper support assembly 14a, lateral lower support assembly 16a, and lateral central joint 12a are all fixed relative to one another and the resulting orthopedic brace 10 functions solely as a splint.

The orthopedic brace 10 further comprises a medial central joint 12b, a medial upper support assembly 14b and a medial lower support assembly 16b, which in combination define a medial longitudinal brace assembly 18b. The construction of the medial longitudinal brace assembly 18b is essentially the same as the lateral longitudinal brace assembly 18a. As such, the medial upper support assembly 14b includes a medial upper support arm 20b and a medial upper housing 22b and the medial lower support assembly 16b similarly includes a medial lower support arm 24b and a medial lower housing 26b. The medial central joint 12b connects the medial upper support assembly 14b with the medial lower support assembly 16b such that the medial upper and lower support assemblies 14b, 16b extend radially from the medial central joint 12b.

The orthopedic brace 10 additionally comprises an upper distal strap retention assembly 34a and an upper proximal strap retention assembly 36a, both of which are associated with the lateral and medial upper support assemblies 14a, 14b. The upper distal strap retention assembly 34a includes an upper distal strap guide member 38a integral with a distal end 40a of the lateral upper housing 22a and an upper distal strap connection member 42a integral with a distal end 40b of the medial upper housing 22b. The upper distal strap guide member 38a has a strap guide loop 44 and a rotationally-connected strap lock 46 positioned adjacent to the strap guide loop 44. The upper distal strap connection member 42a has a strap anchor loop 48 and a strap connection hook 50 positioned on opposite sides of the upper distal strap connection member 42a.

The upper distal strap guide and connection members 38a, 42a are preferably fabricated from a relatively rigid material, such as a high-strength plastic, and have an arcuate configuration, which corresponds to the contours of the body of a user on whom the orthopedic brace 10 is to be mounted in a manner described below. The upper distal strap retention assembly 34a further includes an upper distal strap attachment member 52a likewise preferably fabricated from a relatively rigid high-strength plastic. The upper distal strap attachment member 52a has a strap attachment loop 54 and a strap connection loop 56 positioned on opposite sides of the upper distal strap attachment member 52a.

The upper proximal strap retention assembly 36a includes an upper proximal strap guide member 58a attached to a proximal end 60a of the lateral upper support arm 20a by fasteners 62, such as rivets, and an upper proximal strap connection member 64a attached to a proximal end 60b of the medial upper support arm 20b likewise by fasteners 62. The upper proximal strap retention assembly 36a further includes an upper proximal strap attachment member 66a. The upper proximal strap guide member 58a, upper proximal strap connection member 64a, and upper proximal strap attachment member 66a have essentially the same construction as the upper distal strap guide member 38a, upper distal strap connection member 42a, and upper distal strap attachment member 52a, respectively. Accordingly, components common to corresponding members are designated by the same reference characters.

The orthopedic brace 10 still further comprises a lower distal strap retention assembly 34b and a lower proximal strap retention assembly 36b, each of which is associated with both the lateral and medial lower support assemblies 16a, 16b. The lower distal strap retention assembly 34b is essentially the same as the upper distal strap retention assembly 34a. As such, the lower distal strap retention assembly 34b includes a lower distal strap guide member 38b integral with a distal end 68a of the lateral lower housing 26a, a lower distal strap connection member 42b integral with a distal end 68b of the medial lower housing 26b, and a lower distal strap attachment member 52b.

The lower proximal strap retention assembly 36b is essentially the same as the upper proximal strap retention assembly 36a. As such, the lower proximal strap retention assembly 36b includes a lower proximal strap guide member 58b attached to a proximal end 70a of the lateral lower support arm 24a by fasteners 62, a lower proximal strap connection member 64b attached to a proximal end 70b of the medial lower support arm 24b by fasteners 62, and a lower proximal strap attachment member 66b. The lower distal and lower proximal strap guide members 38b, 58b, lower distal and lower proximal strap connection members 42b, 64b, and lower distal and lower proximal strap attachment members 52b, 66b have essentially the same construction as the upper distal and upper proximal strap guide members 38a, 58a, upper distal and upper proximal strap connection members 42a, 64a, and upper distal and upper proximal strap attachment members 52a, 66a, respectively. Accordingly, components common to corresponding members are designated by the same reference characters.

A pad 72 is preferably provided in association with each upper and lower distal strap guide and connection member 38a, 38b, 42a, 42b and each upper and lower proximal strap guide and connection member 58a, 58b, 64a, 64b. The pads 72 are affixed to the inner face of each of the members 38a, 38b, 42a, 42b, 58a, 58b, 64a, 64b by fastening means (not shown), such as hook and loop fasteners commonly termed VELCRO. The pads 72 cushion the body of the user from the relatively hard, rigid surfaces of the orthopedic brace 10 when the orthopedic brace 10 is mounted on the body.

Figure 2:
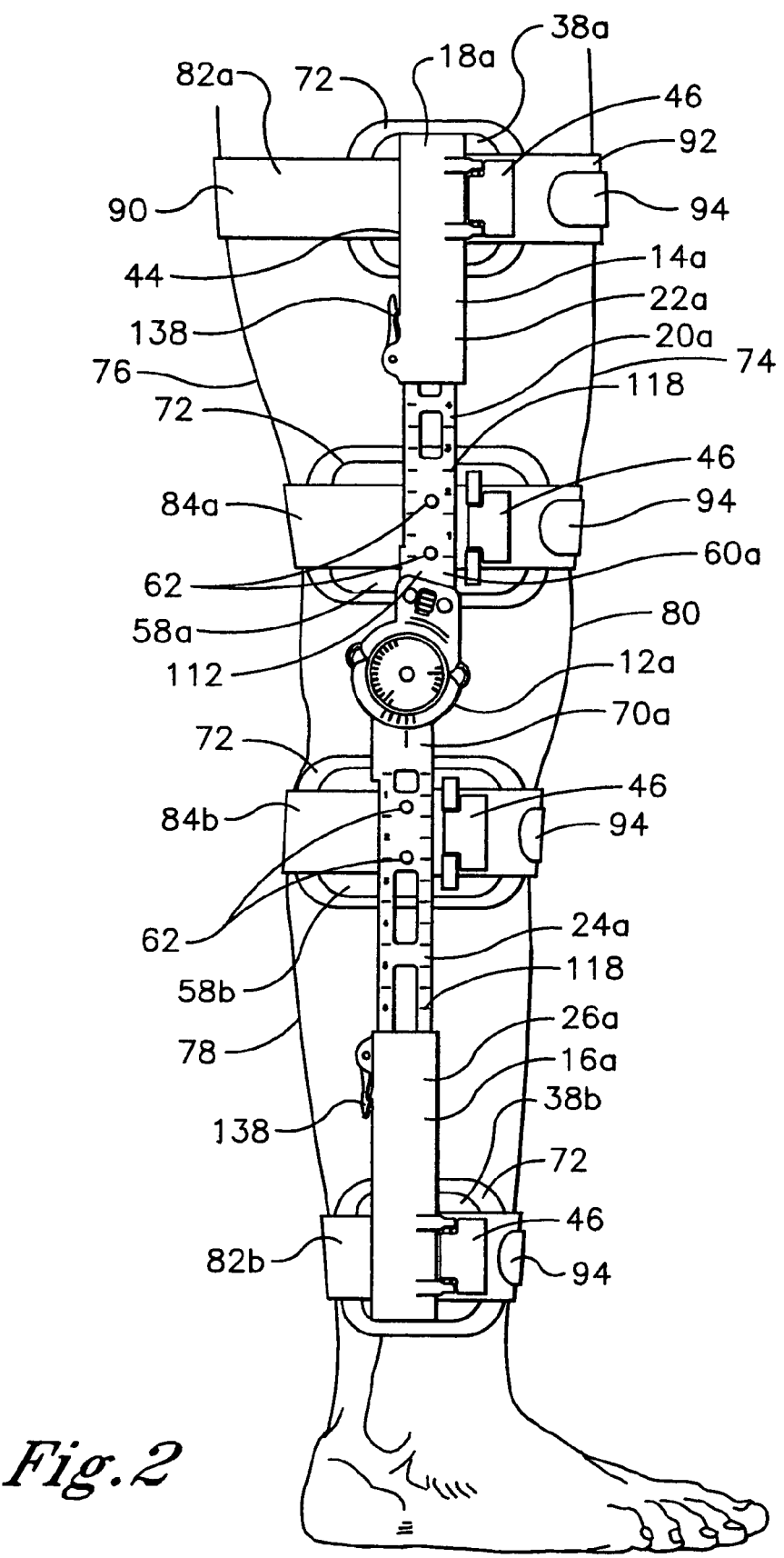
FIG. 2 is a lateral view of the orthopedic brace of FIG. 1 mounted on the leg of a user.
Figure 3:
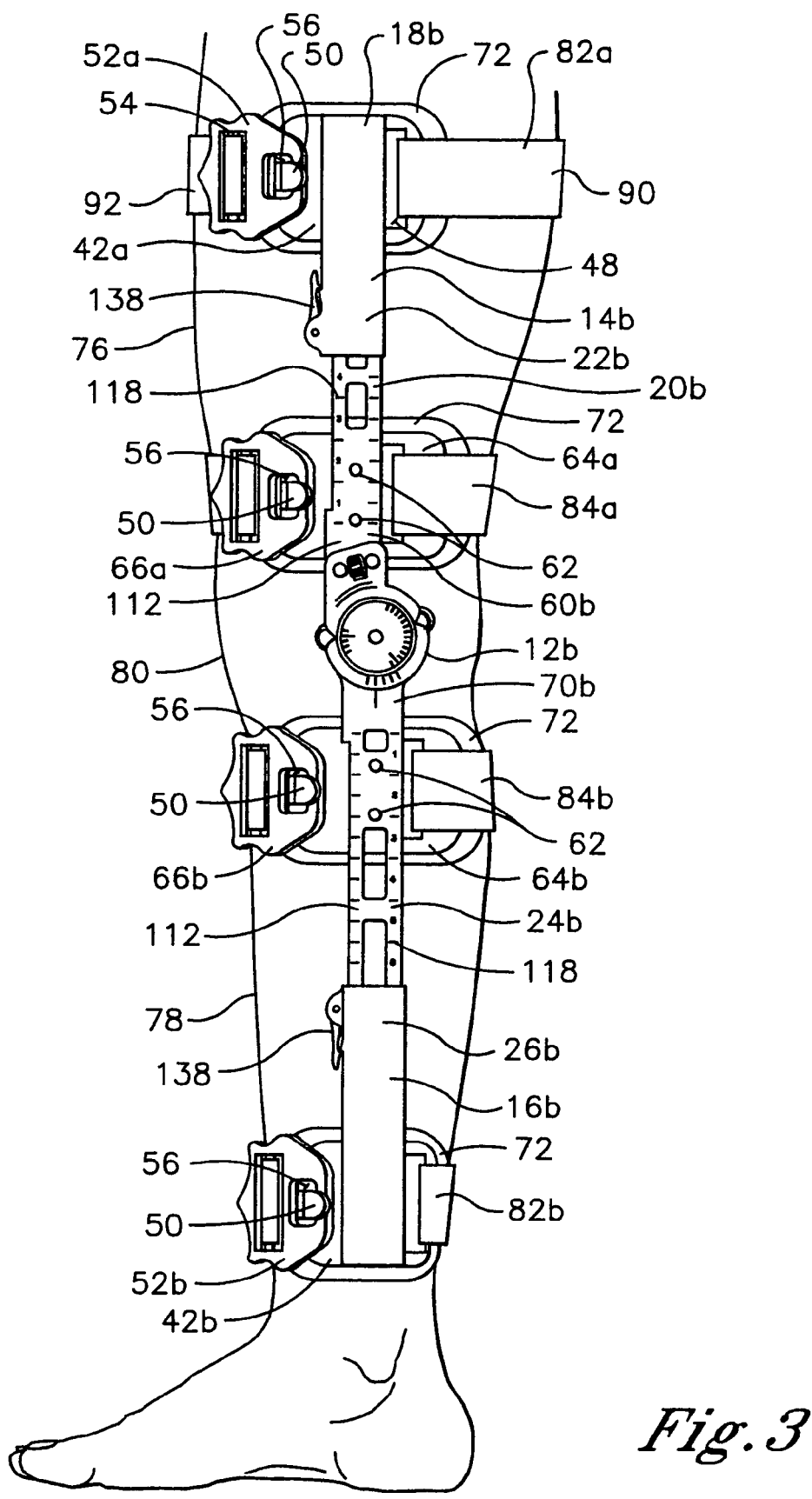
FIG. 3 is a medial view of the orthopedic brace of FIG. 1 mounted on the leg of a user.
Figure 4:
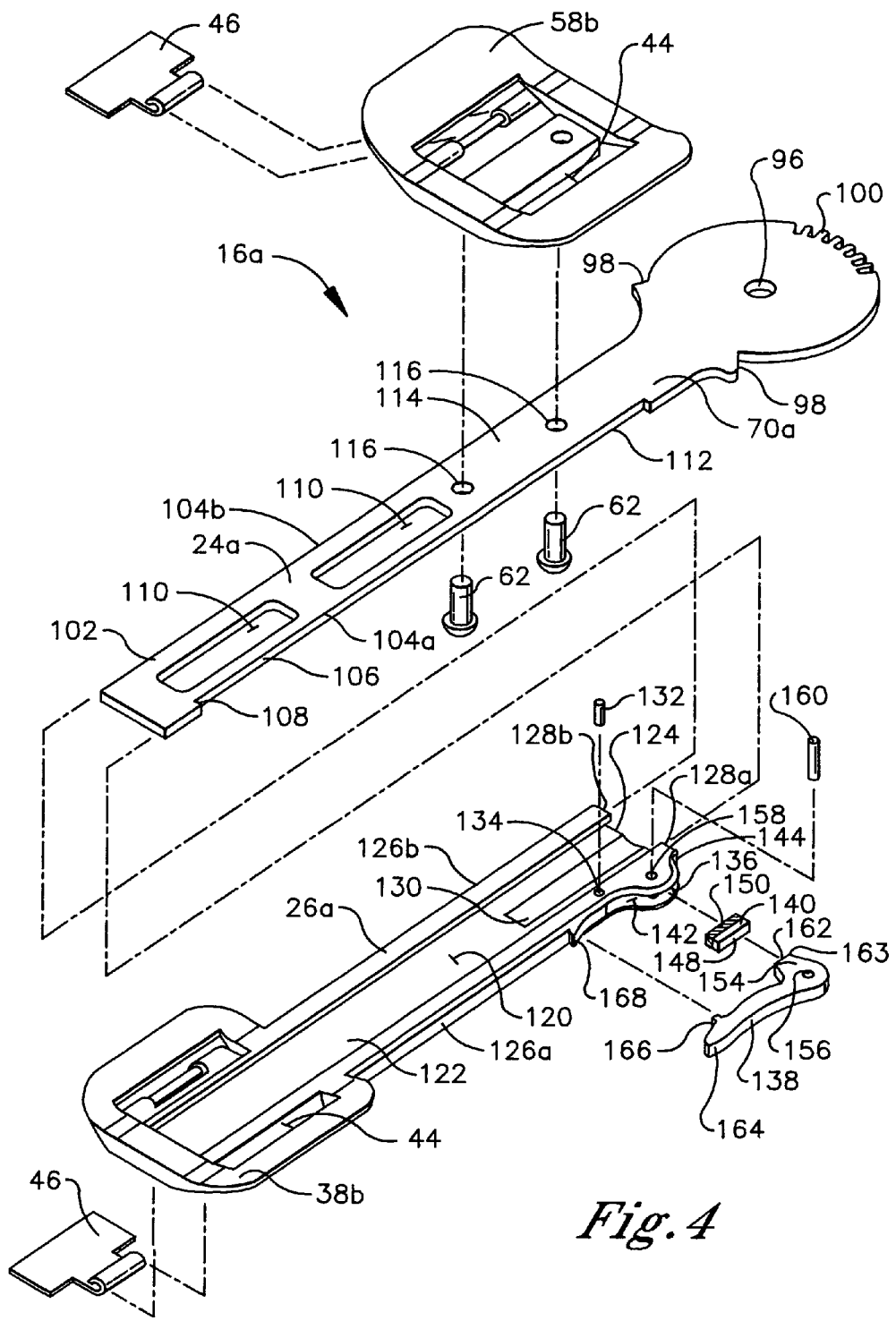
FIG. 4 is an exploded rear perspective view of a support assembly of the orthopedic brace of FIG. 1.

For purposes of illustration, the orthopedic brace 10 shown and described herein is a specific type of orthopedic brace commonly termed a post-operative knee brace. Full utility of the orthopedic brace 10 is achieved when the orthopedic brace 10 is mounted on the leg of a user. Referring additionally to FIGS. 2 and 3, the orthopedic brace 10 is mounted on the right leg 74, which is characterized as having an upper leg 76, a lower leg 78, and a knee joint 80 rotationally connecting the upper and lower legs 76, 78. It will be apparent to the skilled artisan that the post-operative knee brace 10 is likewise adaptable for mounting on the left leg (not shown) of the user.

The orthopedic brace 10 is further provided with a plurality of straps which engage the strap retention assemblies to retain the orthopedic brace 10 on the leg 74 during use. In particular, an upper distal strap 82a engages the upper distal strap retention assembly 34a and an upper proximal strap 84a engages the upper proximal strap retention assembly 36a. A lower distal strap 82b similarly engages the lower distal strap retention assembly 34b and a lower proximal strap 84b engages the lower proximal strap retention assembly 36b.

Engagement of the upper distal strap 82a with the upper distal strap retention assembly 34a is effected by anchoring a first end 86 of the upper distal strap 82a to the strap anchor loop 48 of the upper distal strap connection member 42a by relatively permanent fastening means, such as sewing. The second end 88 of the upper distal strap 82a is threaded through the strap guide loop 44 of the upper distal strap guide member 38a to define a posterior segment 90 of the upper distal strap 82a extending between the upper distal strap connection member 42a and upper distal strap guide member 38a. The length of the posterior segment 90 is adjusted in correspondence with the size of the leg 74 and releasably fixed by fastening the strap lock 46 on the upper distal strap guide member 38a to the upper distal strap 82a using fastening means (not shown), such as hook and loop fasteners mounted on the inner face of the strap lock 46 and outer face of the upper distal strap 82a. As such, the posterior segment 90 of the upper distal strap 82a posteriorly connects the lateral and medial longitudinal brace assemblies 18a, 18b.

The second end 88 of the upper distal strap 82a extending from the upper distal strap guide member 38a is threaded through the strap attachment loop 54 of the upper distal strap attachment member 52a to define an anterior segment 92 of the upper distal strap 82a extending between the upper distal strap guide member 38a and upper distal strap attachment member 52a. The length of the anterior segment 92 is adjusted in correspondence with the size of the leg 74 and releasably fixed by doubling the second end 88 back over the upper distal strap 82a. A fastening tab 94 attached to the second end 88 provides fastening means, such as hook and loop fasteners, for fastening the second end 88 onto the upper distal strap 82a. With the orthopedic brace 10 mounted on the leg 74, the anterior segment 92 of the upper distal strap 82a and the upper distal strap attachment member 52a are drawn away from the upper distal strap guide member 38a across the anterior of the upper leg 76 to the upper distal strap connection member 42a, where the strap connection loop 56 of the upper distal strap attachment member 52a loops over the strap connection hook 50 of the upper distal strap connection member 42a. As such, the anterior segment 92 of the upper distal strap 82a anteriorly connects the lateral and medial longitudinal brace assemblies 18a, 18b. Thus, the posterior and anterior segments 90, 92 of the upper distal strap 82a in combination completely encircle the leg 74.

Engagement of the lower distal strap 82b with the lower distal strap retention assembly 34b, the upper proximal strap 84a with the upper proximal strap retention assembly 36a, and the lower proximal strap 84b with the lower proximal strap retention assembly 36b is effected in a substantially similar manner as described above with respect to the upper distal strap 82a and upper distal strap retention assembly 34a. As such, the upper distal strap 82a, lower distal strap 82b, upper proximal strap 84a, and lower proximal strap 84b closely secure the orthopedic brace 10 to the leg 74 of the user.

When the orthopedic brace 10 is properly mounted on and closely secured to the leg 74, the lateral central joint 12a is positioned adjacent to the lateral side of the knee joint 80 and the medial central joint 12b is positioned adjacent to the medial side of the knee joint 80. The lateral upper longitudinal support assembly 14a is positioned adjacent to the lateral side of the upper leg 76 is longitudinally aligned with the lateral side of the upper leg 76. The medial upper longitudinal support assembly 14b is positioned adjacent to the medial side of the upper leg 76 and is longitudinally aligned with the medial side of the upper leg 76. The lateral lower longitudinal support assembly 16a is similarly positioned adjacent to the lateral side of the lower leg 78 and is longitudinally aligned with the lateral side of the lower leg 78. The medial lower longitudinal support assembly 16b is positioned adjacent to the medial side of the lower leg 78 and is longitudinally aligned with the medial side of the lower leg 78.

Referring to FIGS. 4-7, the lateral lower support assembly 16a and associated strap guide members 38b, 58b are shown and described hereafter in greater detail. As recited above, the lateral lower support assembly 16a includes a lateral lower support arm 24a and a lateral lower housing 26a. Both are preferably fabricated from lightweight, high-strength, relatively rigid materials. The lateral lower support arm 24a is more preferably fabricated from a metal, such as aluminum or stainless steel, and the lateral lower housing 26a is more preferably fabricated from a molded plastic. The proximal end 70a of the lateral lower support arm 24a is configured to cooperatively engage the lateral central joint 12a. For example, if the lateral central joint 12a is a releasably locking rotational hinge as shown herein, the proximal end 70a is preferably configured with a hinge pivot aperture 96 to enable rotation of the lateral lower support arm 24a about the lateral central joint 12a and with a plurality of rotation limiting faces 98 and rotation lock notches 100 to enable the rotation limiting and rotation locking functions of the hinge, respectively. Notwithstanding the above, it is understood that the proximal end 70a of the lateral lower support arm 24a is not limited to any one specific configuration, but can have any number of alternate configurations, which cooperatively correspond with the particular function, construction and configuration of the lateral central joint 12a.

The remainder of the lateral lower support arm 24a, extending from the proximal end 70a to a distal end 102, has an elongate bar-like configuration with first and second longitudinal edges 104a, 104b on opposite sides of the lateral lower support arm 24a. The first longitudinal edge 104a is essentially linear, but has a shallow indentation 106 extending along the majority of its length. The indentation 106 extends from immediately adjacent to the tip of the distal end 102 toward the proximal end 70a of the lateral lower support arm 24a. The distal terminus of the indentation 106 defines a step which provides the lateral lower support arm 24a with a travel stop 108. The second longitudinal edge 104b is likewise linear, but in contrast to the first longitudinal edge 104a is smooth and continuous along its entire length.

A plurality of cut-outs 110 are formed through entire thickness of the lateral lower support arm 24a, thereby extending from the outer face 112 to the inner face 114 of the lateral lower support arm 24a. The cut-outs 110 reduce the weight of the lateral lower support arm 24a and correspondingly reduce the overall weight of the orthopedic brace 10 without significantly diminishing the structural strength and integrity of the lateral lower support arm 24a. Fastening apertures 116 are also formed through the entire thickness of the lateral lower support arm 24a, which enable attachment of the lower proximal strap guide member 58b to the lateral lower support arm 24a by means of the fasteners 62. The outer face 112 of the lateral lower support arm 24a is provided with a plurality of graduated length markers 118 (shown in FIGS. 1-3), which enable the user to determine the selected length of the lateral lower support assembly 16a as described below.

The lateral lower housing 26a includes a length-adjusting mechanism for guiding sliding displacement of the lateral lower support arm 24a relative to the lateral lower housing 26a and a locking mechanism for selectively preventing sliding displacement of the lateral lower support arm 24a. The length-adjusting mechanism comprises a travel track 120 formed in and partially enclosed by the lateral lower housing 26a. The front of the travel track 120 is bounded by an inner face 122 of the lateral lower housing 26a. The distal end of the travel track 120 is bounded by the distal end 68a of the lateral lower housing 26a, while the proximal end of the travel track corresponds to a proximal end 124 of the lateral lower housing 26a, which is open and unbounded.

The sides of the travel track 120 are bounded by first and second rails 126a, 126b, which extend from the inner face 122 in an essentially perpendicular direction. A first lip 128a extends perpendicularly from the first rail 126a and a second lip 128b likewise extends perpendicularly from the second rail 126b. The first and second lips 128a, 128b each project over a portion of the inner face 122 of the lateral lower housing 26a on opposite sides thereof to partially bound the back of the travel track 120 while the remainder of the back of the travel track 120 is open. Thus, the first rail 126a and first lip 128a in combination and the second rail 126b and second lip 128b in combination each has the configuration of an inverted "L".

The lateral lower support arm 24a is telescopingly fitted within the travel track 120 for slidable displacement therein. In particular, the lateral lower support arm 24a is positioned in the travel track 120 of the lateral lower housing 26a such that the outer face 112 of the lateral lower support arm 24a is adjacent to the inner face 122 of the lateral lower housing 26a, the first and second longitudinal edges 104a, 104b are adjacent to the first and second rails 126a, 126b, respectively, and the inner face 114 is adjacent to the first and second lips 128a, 128b. The width of the inner face 122 is at least slightly greater than the width of the lateral lower support arm 24a at its widest point within the travel track 120 (typically at the travel stop 108) and the height of the first and second rails 126a, 126b (i.e., the distance from the inner face 122 to the inside of the first and second lips 128a, 128b) is at least slightly greater than the thickness of the lateral lower support arm 24a. A clearance slot 130 is formed in the inner face 122 of the lateral lower housing 26a, which enables the heads of the fasteners 62 on the lateral lower support arm 24a to clear the inner face 122 of the lateral lower housing 26a.

Slidable displacement of the lateral lower support arm 24a within the travel track 120 is distally constrained by the closed distal end 68a of the lateral lower housing 26a in cooperation with the distal end 102 of the lateral lower support arm 24a and is proximally constrained by the travel stop 108 of the lateral lower support arm 24a in cooperation with a travel limit post 132 positioned in the travel track 120. The travel limit post 132 extends into the travel track 120 via a post aperture 134 formed through the first lip 128a. The travel limit post 132 and travel stop 108 prevent the user from inadvertently withdrawing the lateral lower support arm 24a in its entirety from the travel track 120 via the open proximal end 124 of the lateral lower housing 26a when slidably displacing the lateral lower support arm 24a in the proximal direction within the travel track 120. The closed distal end 68a of the lateral lower housing 26a stops the distal end 102 of the lateral lower support arm 24a when slidably displacing the lateral lower support arm 24a in the distal direction within the travel track 120.

The locking mechanism comprises a lock chamber 136 and a lock lever 138. FIGS. 4-10 show a specific embodiment of the locking mechanism which further comprises an optional friction plate 140. The lock chamber 136 is formed in the first rail 126a of the lateral lower housing 26a. The lock chamber 136 is open to the exterior of the lateral lower housing 26a via an external opening 142 which is bounded on opposite sides by sidewalls 144. The lock chamber 136 is also open to the travel track 120 via an internal opening 146.

The friction plate 140 has a laminate construction. A first layer 148 of the friction plate 140 is preferably formed from a rigid non-compressible material, such as a metal. A second layer 150 of the friction plate 140 is preferably formed from a material having a relatively high coefficient of static friction in association with the material of the lateral lower support arm 24a, such as an elastically compressible material and more particularly an elastomer.

The friction plate 140 is sized in correspondence with the lock chamber 136 and internal opening 146 to enable fitted positioning of the friction plate 140 within the lock chamber 136 and internal opening 146. In particular, the length and width of the friction plate 140 are at least slightly smaller than the length and width of the internal opening 146 so that the friction plate 140 fits within the internal opening 146 when the friction plate 140 is positioned in the lock chamber 136. The friction plate 140 is preferably oriented in the lock chamber 136 such that the first layer 148 faces the lock lever 138 while the second layer 150 extends through the internal opening 146 and faces the lateral lower support arm 24a housed in the travel track 120. As such, the internal opening 146 enables the second layer 150 to engage the lateral lower support arm 24a and, more particularly, enables the friction plate 140 to selectively press against the indentation 106 in the first longitudinal edge 104a of the lateral lower support arm 24a when a sufficient pressing force is applied to the friction plate 140 in the direction of the travel track 120 as described hereafter.

The lock lever 138 includes a head 154 having an oblong configuration. A lever pivot aperture 156 is formed through the head 154 and lever pivot apertures 158 are formed through the sidewalls 144 of the lock chamber 136. The lever pivot apertures 156, 158 are all aligned with one another and a lever pivot pin 160 is fitted through the apertures 156, 158 and retained therein to enable manual rotation of the head 154 within the lock chamber 136 about the lever pivot pin 160. Accordingly, the head 154 is rotationally displaceable relative to the friction plate 140 and lateral lower support arm 24a.

Figure 5:
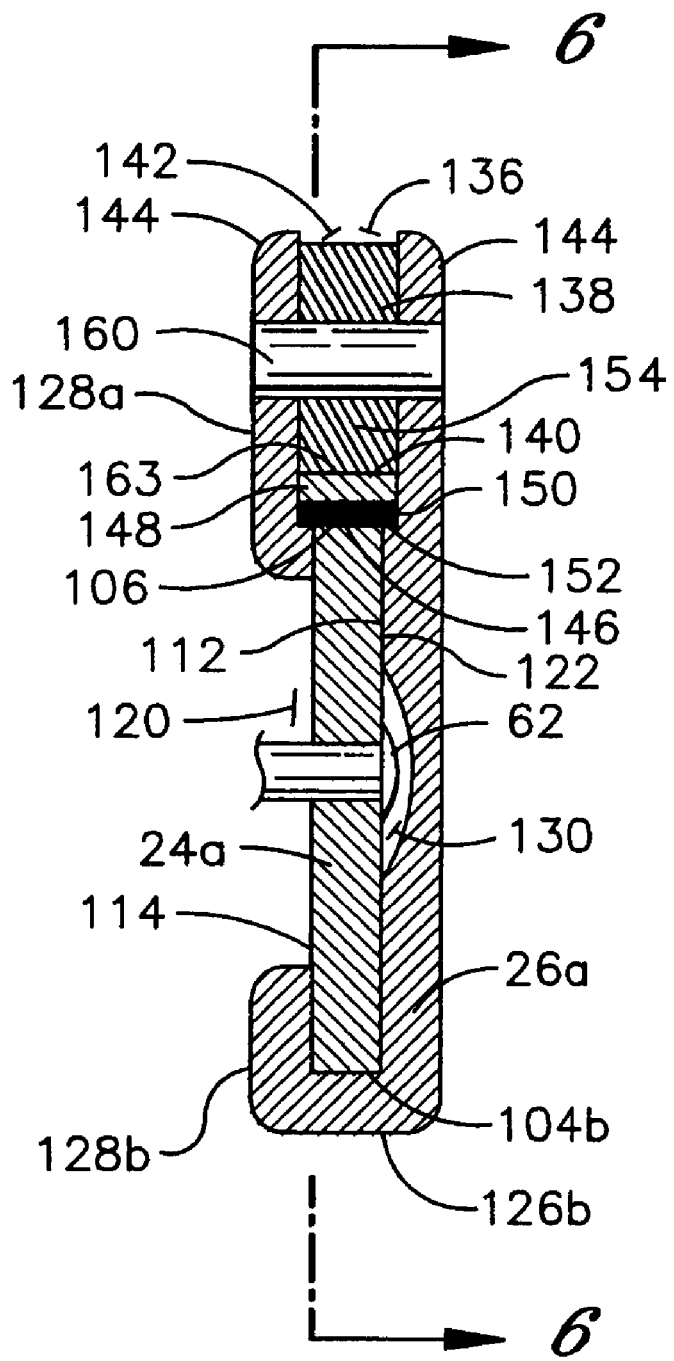
FIG. 5 is detailed cross-sectional view of the locking mechanism in the support assembly of FIG. 4, which is taken along line 5-5 (shown in FIG. 6), wherein the locking mechanism is in a closed position.

The oblong-shaped head 154 has an elongated end 162 termed a force applicator which has a relatively straight flat surface bounded on one side by a leading edge 163. When the head 154 is rotationally positioned such that the force applicator 162 is adjacent the first layer 148 of the friction plate 140, the elongated force applicator 162 engages the first layer 148 and applies a pressing force to the friction plate 140 and the underlying lateral lower support arm 24a. This cooperative arrangement of the components of the locking mechanism is termed the locked or closed position and is shown in FIGS. 5 and 6. The configuration of the head 154, the pressing force of the head 154 against the friction plate 140, and the friction forces between the head 154 and friction plate 140 enable the head 154 to resist rotational displacement in the clockwise direction (when viewed from the front rather than from the rear as in FIGS. 4 and 6) and enable the locking mechanism to maintain the closed position in the absence of any overriding external rotational forces applied to the lock lever 138 in the clockwise direction.

The components of the locking mechanism are selectively repositionable from the closed position to a second cooperative arrangement termed the open or unlocked position shown in FIG. 7 by applying a sufficient overriding external rotational force to the lock lever 138 to overcome the resistance of the head 154 to rotational displacement. In particular, an overriding external rotational force is applied to the lock lever 138 in the clockwise direction which is sufficient to rotate the head 154 in a clockwise direction from the closed position until the leading edge 163 clears the friction plate 140. The locking mechanism achieves the open position when the force applicator 162 disengages from the first layer 148 of the friction plate 140, thereby reducing the pressing force of the head 154 on the friction plate 140, and preferably fully withdrawing the pressing force from the friction plate 140. The locking mechanism is selectively returned to the closed position by applying an external rotational force to the lock lever 138 in a counter-clockwise direction until the leading edge 163 passes the friction plate 140 and the force applicator 162 is again adjacent the first layer 148, thereby engaging the first layer 148 and applying a pressing force to the friction plate 140 and the underlying lateral lower support arm 24a.

The lock lever 138 also has a lever arm 164 attached to the head 154. The lever arm 164 extends through the external opening 142 out of the lock chamber 136. A first lock catch 166 is integrally formed on the side of the lever arm 164 facing the lateral lower housing 26a. A cooperative second lock catch 168 is likewise integrally formed on the lateral lower housing 26a in correspondence with the first lock catch 166. When the locking mechanism is in the closed position, the first and second lock catches 166, 168 are in press-fitting engagement with one another to additionally resist rotational displacement of the head 154 in the clockwise direction and to provide a visual indicator that the locking mechanism is in the closed position. When the overriding external rotational force is applied to the lock lever 138 sufficient to rotate the head 154 in the clockwise direction, the first and second lock catches 166, 168 are simultaneously released from press-fitting engagement with one another.

The construction of the lateral and medial upper support assemblies 14a, 14b and medial lower support assembly 16b is essentially the same as the construction of the lateral lower support assembly 16a. Accordingly, the above-recited description of the lateral lower support assembly 16a applies equally to the remaining support assemblies 14a, 14b, 16b.

Figure 8:
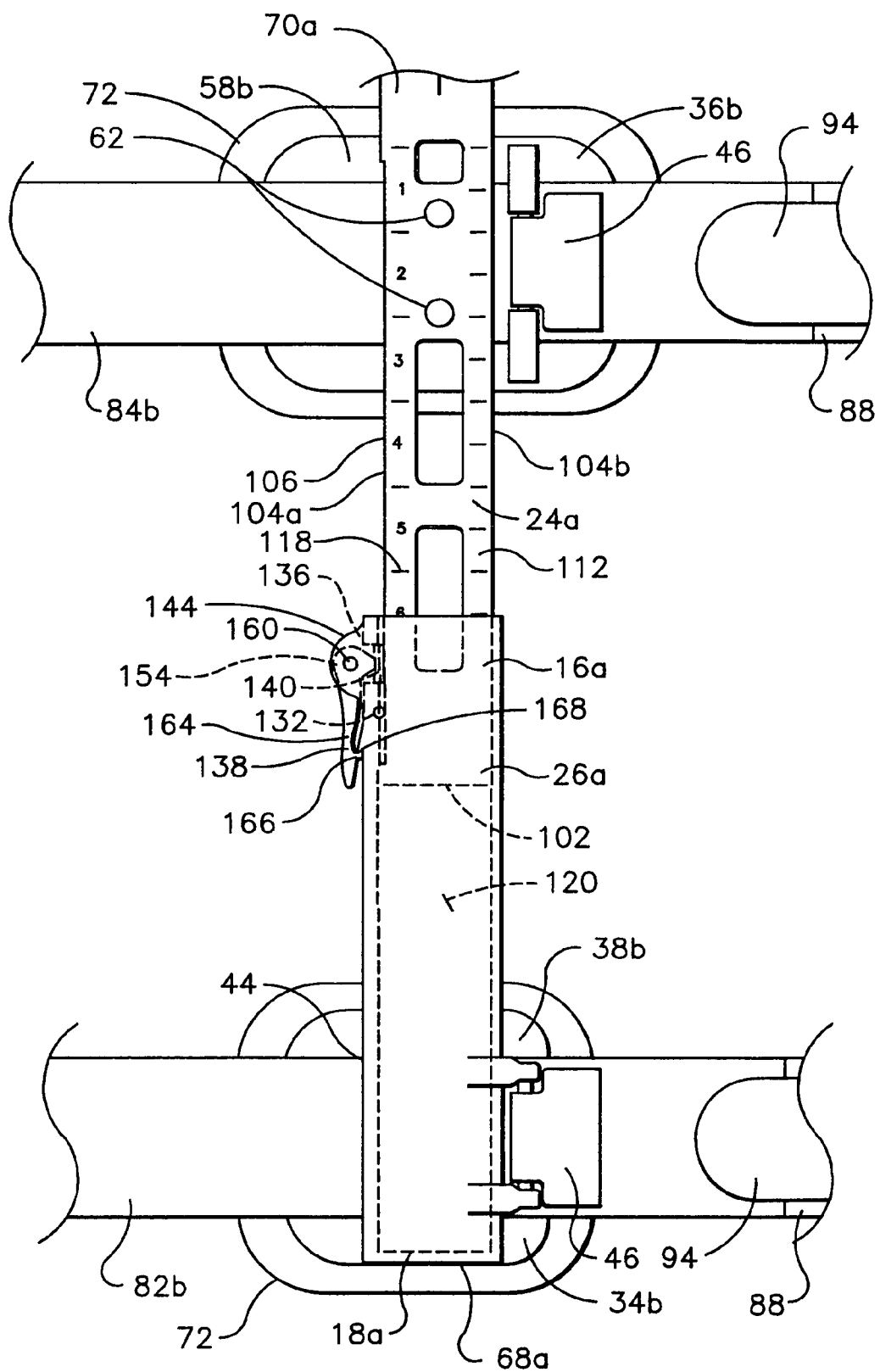
FIG. 8 is a front elevational view of the support assembly of FIG. 4 in a locked mode of operation, wherein the support assembly is fixed at a first selected length.

Exemplary operation of a support assembly of the orthopedic brace 10 is shown and described below in greater detail with reference to the lateral lower support assembly 16a and FIGS. 8-10. Referring initially to FIG. 8, the lateral lower support assembly 16a is in a locked mode of operation. Accordingly, the locking mechanism of the lateral lower support assembly 16a is in a closed position, which fixes the length of the lateral lower support assembly 16a. In the present case, the length of the lateral lower support assembly 16a is fixed at a first selected length, which is an extended length similar to that shown in FIG. 1 at or near the upper length limit of the lateral lower support assembly 16a.

In accordance with the closed position, the first lock catch 166 on the lever arm 164 and the second lock catch 168 on the lateral lower housing 26a are press fitted together and the force applicator 162 on the head 154 of the lock lever 138 engages the first layer 148 of the friction plate 140, thereby applying a pressing force to the friction plate 140 in the direction of the travel track 120. The pressing force causes the second layer 150 of the friction plate 140 to press against the indentation 106 in the first longitudinal edge 104a of the lateral lower support arm 24a with a substantial force. This force, coupled with the relatively high coefficient of static friction for the materials of the second layer 150 and lateral lower support arm 24a, essentially prevents slidable displacement of the lateral lower support arm 24a in either direction within the travel track 120 when subjected to normally encountered operational forces, thereby maintaining the length of the lateral lower support assembly 16a fixed at the first selected length.

Figure 9:
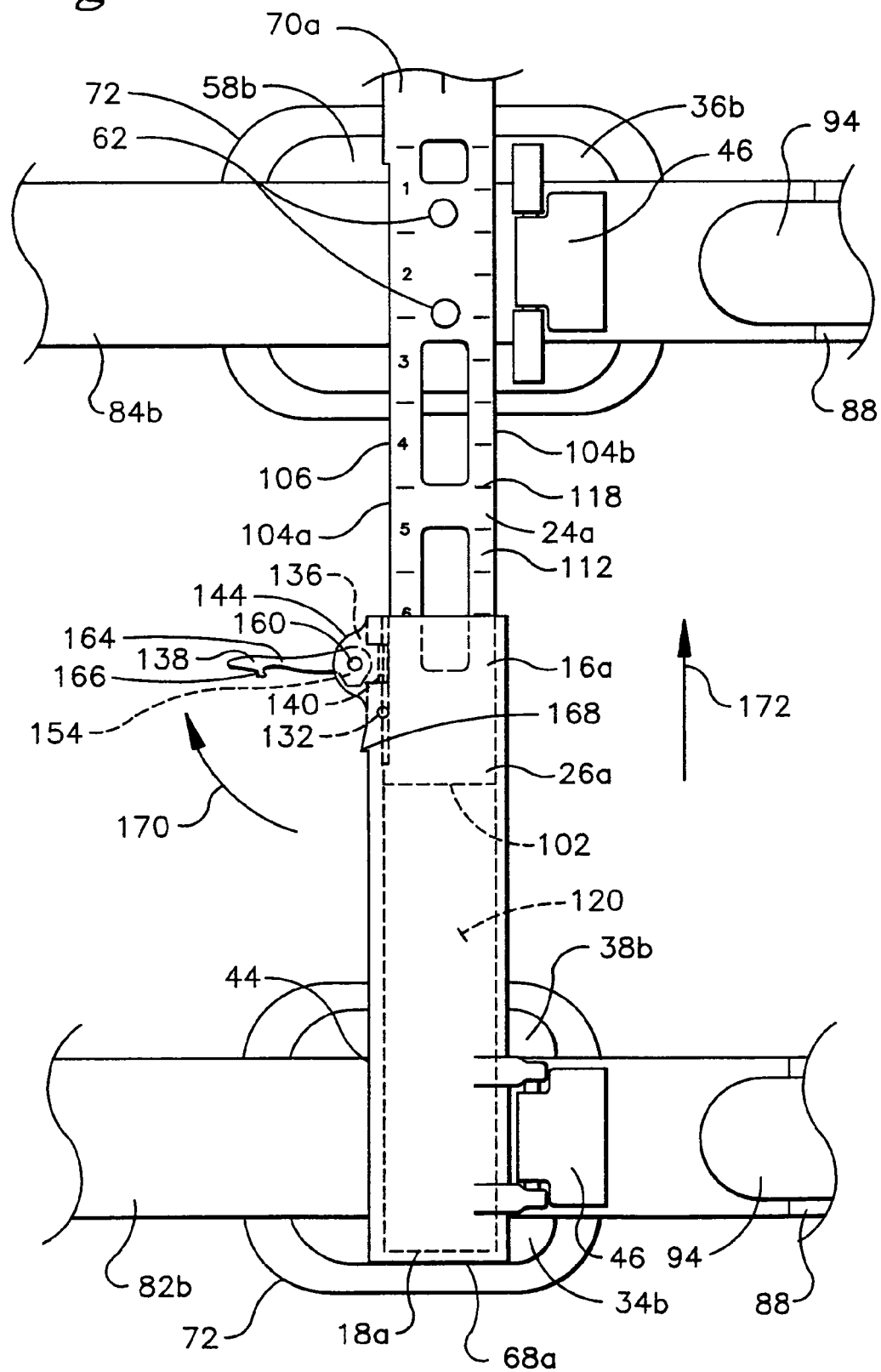
FIG. 9 is a front elevational view of the support assembly of FIG. 4 in an adjustment mode of operation, wherein the support assembly is adjustable to an alternate selected length.

Referring to FIG. 9, the lateral lower support assembly 16a is in an adjustment mode of operation. The locking mechanism has been transitioned to an open position, which correspondingly enables operation of the length-adjusting mechanism of the lateral lower support assembly 16a. The locking mechanism is transitioned to the open position by manually applying an overriding external rotational force to the lever arm 164 in the clockwise direction of arrow 170 which is sufficient to overcome the resistance of the head 154 to rotational displacement. Rotational displacement of the lever arm 164 and head 154 in the clockwise direction releases the first lock catch 166 from the second lock catch 168 and correspondingly disengages the force applicator 162 from the first layer 148 of the friction plate 140, which causes the pressing force to be withdrawn from the friction plate 140 and underlying lateral lower support arm 24a. Accordingly, there is no longer a sufficient force to prevent linear displacement of the lateral lower support arm 24a within the travel track the 120 when subjected to relatively low linear displacement forces.

The length-adjusting mechanism permits a user to select an alternate length of the lateral lower support assembly 16a different than the first selected length when the locking mechanism is in the open position. For example, it may be desirable to adjust the length of the lateral lower support assembly 16a from the extended first selected length to a second selected length, which is a shortened length, i.e., shorter than extended length. The length of the lateral lower support assembly 16a is adjusted to the second selected length preferably by removing the orthopedic brace from the leg, if this has not already been done prior to the locking mechanism transitioning step. A sufficient upward linear displacement force is manually applied to the lateral lower housing 26a, which in the present case is in the direction of arrow 172, to slidably displace the lateral lower support arm 24a within the travel track 120 and telescope the lateral lower support arm 24a into the lateral lower housing 26a.

Figure 10:
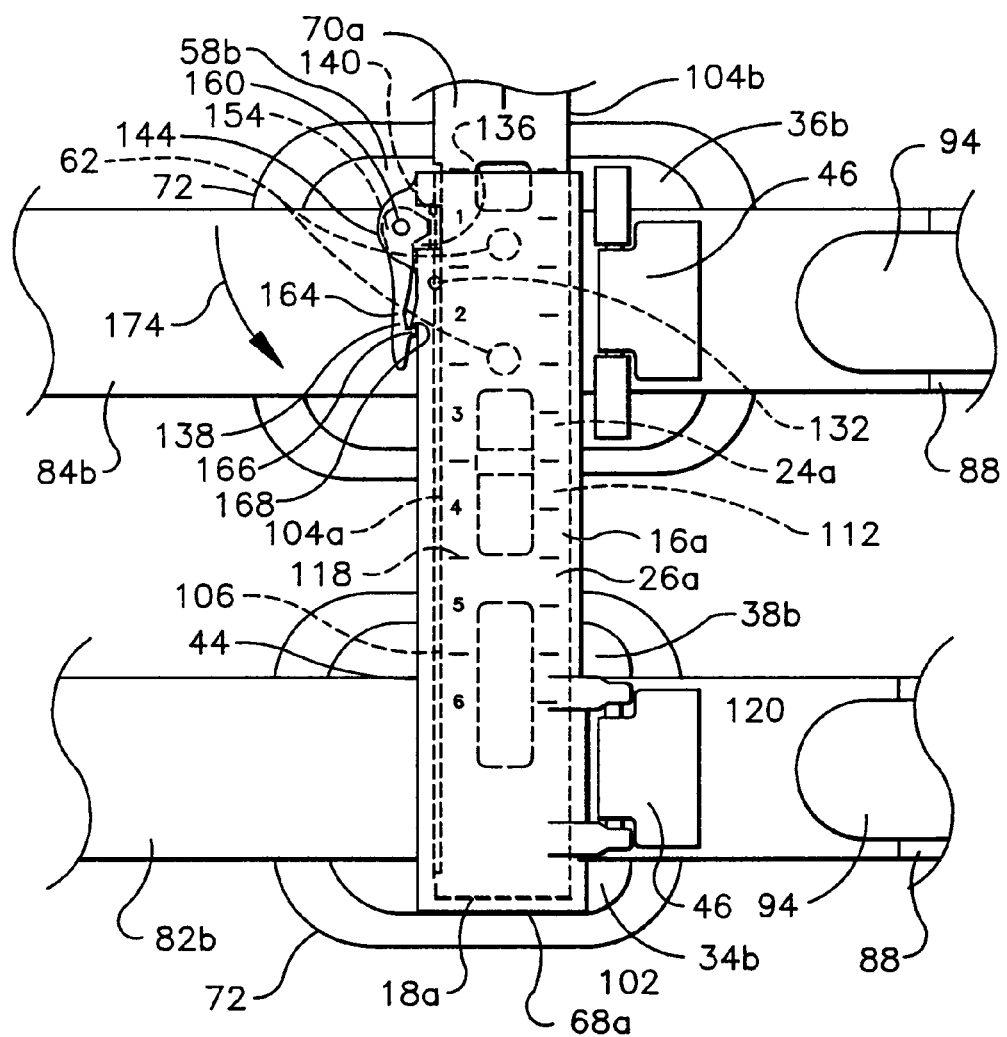
FIG. 10 is a front elevational view of the support assembly of FIG. 4 in the locked mode of operation, wherein the support assembly has been adjusted to a second selected length.

Referring to FIG. 10, the lateral lower support assembly 16a is transitioned back to the locked mode of operation after completing the length adjusting step so that the orthopedic brace may be remounted on the leg. The locking mechanism of the lateral lower support assembly 16a is shown again in the closed position, which essentially prevents linear displacement of the lateral lower support arm 24a in either direction within the travel track the 120. In the present case, the length of the lateral lower support assembly 16a is fixed at the second selected length, which was selected in the length adjusting step near the lower length limit of the lateral lower support assembly 16a where the lower distal strap guide member 38a approaches the lower proximal strap guide member 58a.

The locking mechanism is retransitioned to the closed position by reversing the locking mechanism transitioning step described above. In particular, the lever arm 164 and correspondingly the head 154 are manually rotated in the counter-clockwise direction of arrow 174 until the leading edge 163 of the force applicator 162 passes the friction plate 140 and the force applicator 162 is adjacent to and engaging the first layer 148 of the friction plate 140. The first and second lock catches 166, 168 are also press fitted together. The resulting position of the lever arm 164 and head 154 applies a sufficient pressing force to the friction plate 140 and underlying lateral lower support arm 24a to prevent linear displacement of the lateral lower support arm 24a in either direction within the travel track the 120, thereby maintaining the length of the lateral lower support assembly 16a fixed at the second selected length.

Operation of the lateral and medial upper support assemblies 14a, 14b and medial lower support assembly 16b is essentially the same as operation of the lateral lower support assembly 16a. Accordingly, the above-recited description of operation of the lateral lower support assembly 16a applies equally to the remaining support assemblies 14a, 14b, 16b. In general, it is desirable to fix a selected length of both the lateral and medial upper support assemblies 14a, 14b which is essentially equal and to correspondingly fix a selected length of both the lateral and medial lower support assemblies 16a, 16b which is essentially equal. However, the selected length of the upper support assemblies 14a, 14b need not be fixed equal to the selected length of the lower support assemblies 16a, 16b. Indeed, in many instances, the selected length of the upper support assemblies 14a, 14b is substantially shorter than the fixed length of the lower support assemblies 16a, 16b.

Figure 11:
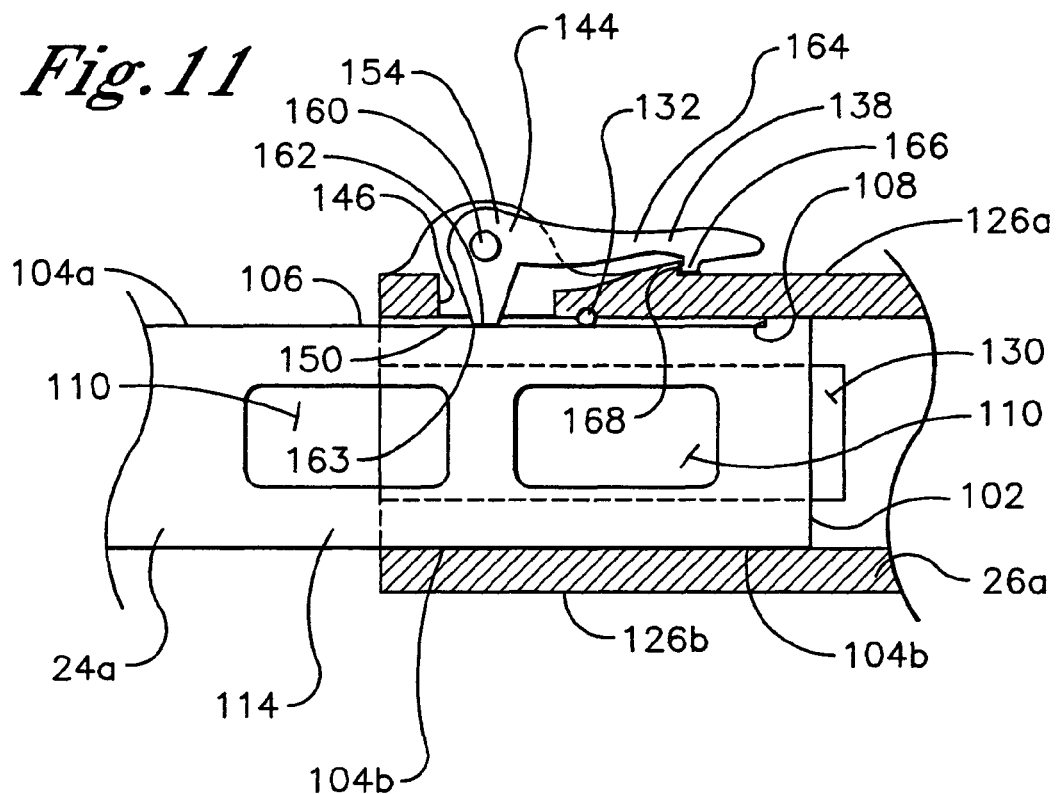
FIG. 11 is a detailed cross-sectional view of an alternate embodiment of a locking mechanism having utility in the support assemblies of the orthopedic brace of FIG. 1, wherein the locking mechanism is in the closed position.
Figure 12:
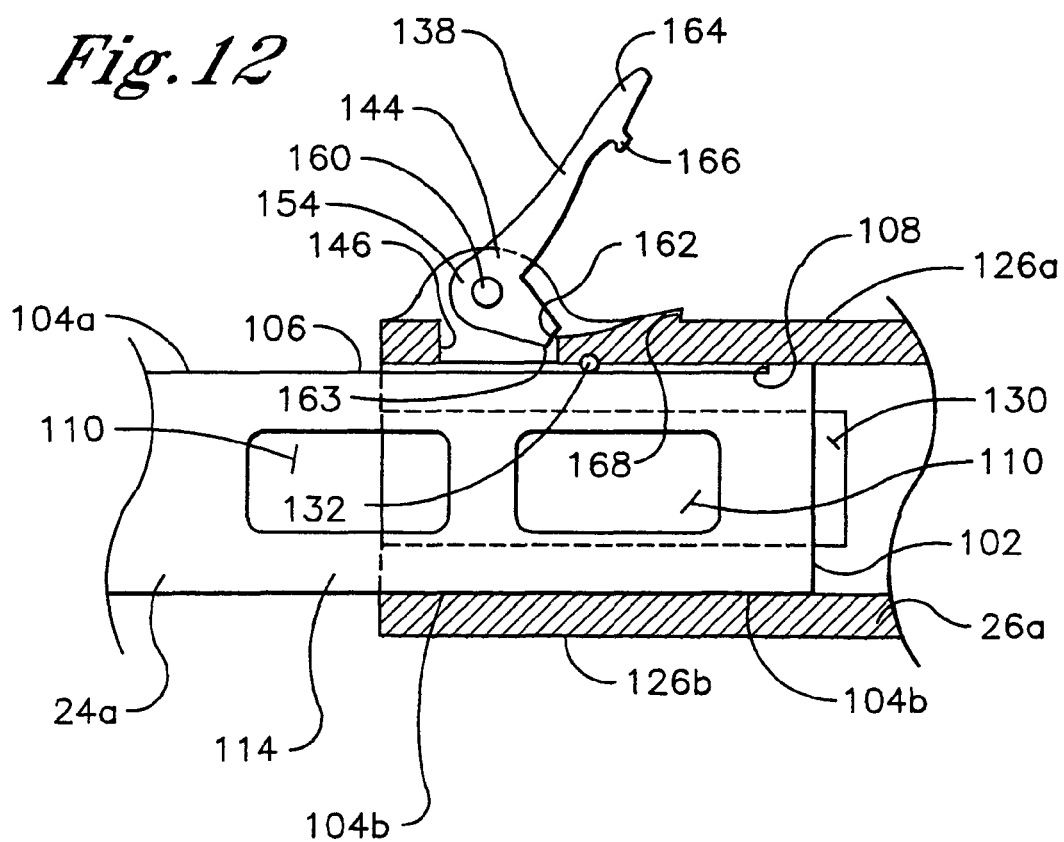
FIG. 12 is a detailed cross-sectional view of the locking mechanism of FIG. 11, wherein the locking mechanism is in the open position.

An alternate embodiment of the locking mechanism having utility in the support assemblies of the orthopedic brace shown in FIGS. 1-3 is described hereafter with reference to FIGS. 11 and 12. The locking mechanism of the present alternate embodiment is substantially the same as the previous embodiment shown in FIGS. 4-10 except that the present locking mechanism omits the friction plate. Accordingly, the elements of FIGS. 11 and 12, which are common to FIGS. 4-10, are denoted by the same reference characters.

The present locking mechanism comprises a lock chamber 136 and a lock lever 138. The lock chamber 136 is formed in the lateral lower housing 26a and has an internal opening 146. The lock lever 138 includes an oblong-shaped head 154 and a lever arm 164 which are rotationally displaceable relative to the lateral lower support arm 24a. The head 154 is sized in correspondence with the lock chamber 136 and internal opening 146 to enable fitted positioning of the head 154 within the lock chamber 136 and internal opening 146. In particular, the head 154 has a force applicator 162 with a length and width at least slightly smaller than the length and width of the internal opening 146 so that the force applicator 162 fits within the internal opening 146 when the head 154 is positioned in the lock chamber 136. The head 154 is preferably oriented in the lock chamber 136 such that the force applicator 162 extends through the internal opening and faces the lateral lower support arm 24a housed in the travel track 120. As such, the internal opening 146 enables the force applicator 162 to engage the lateral lower support arm 24a and, more particularly, enables the force applicator 162 to selectively press directly against the indentation 106 in the first longitudinal edge 104a of the lateral lower support arm 24a in the direction of the travel track 120.

When the head 154 is rotationally positioned such that the force applicator 162 is adjacent the lateral lower support arm 24a, the force applicator 162 engages the lateral lower support arm 24a and applies a pressing force thereto. This cooperative arrangement of the components of the locking mechanism is termed the locked or closed position and is shown in FIG. 11. The configuration of the head 154, the pressing force of the head 154 against the lateral lower support arm 24a, and the friction forces between the head 154 and lateral lower support arm 24a enable the head 154 to resist rotational displacement in the clockwise direction (when viewed from the front rather than from the rear as in FIG. 11) and enable the locking mechanism to maintain the closed position in the absence of any overriding external rotational forces applied to the lock lever 138 in the clockwise direction.

The components of the locking mechanism are selectively repositionable from the closed position to a second cooperative arrangement termed the open or unlocked position shown in FIG. 12 by applying a sufficient overriding external rotational force to the lock lever 138 to overcome the resistance of the head 154 to rotational displacement. In particular, an overriding external rotational force is applied to the lock lever 138 in a clockwise direction which is sufficient to rotate the head 154 in a clockwise direction from the closed position until the leading edge 163 of the force applicator 162 clears the lateral lower support arm 24a. The locking mechanism achieves the open position when the force applicator 162 disengages from the lateral lower support arm 24a, thereby reducing the pressing force of the head 154 on the lateral lower support arm 24a, and preferably fully withdrawing the pressing force from the lateral lower support arm 24a. The locking mechanism is selectively returned to the closed position by applying an external rotational force to the lock lever 138 in a counter-clockwise direction until the leading edge 163 passes the lateral lower support arm 24a and the force applicator 162 is again adjacent the lateral lower support arm 24a, thereby engaging the lateral lower support arm 24a and applying a pressing force thereto.

Although the brace components of the present invention have been described above for purposes of illustration as applying to a post-operative knee brace, it is apparent from the foregoing that the above-recited brace components are readily adaptable to other types of orthopedic braces for the knee or other joints of the body in addition to post-operative knee braces. It is additionally noted that each set of upper support arm, central joint, and lower support arm in the embodiment of the post-operative knee brace described above is a series discrete interconnected components. However, in accordance with an alternate embodiment of the present invention not shown, either the upper support arm or the lower support arm can be integrally formed with the central joint as a continuous structure, which cooperatively functions with the remaining non-integrated support arm. In accordance with another alternate embodiment of the present invention not shown, the position of any housing and correspondingly paired support arm can be reversed so that the upper housing and/or lower housing is more proximal to the central joint than the correspondingly paired upper and/or lower support arm. As such the housing is attached to or integral with the central joint rather than the correspondingly paired support arm, although the support arm remains slidably displaceable within the housing. In accordance with yet another alternate embodiment of the present invention not shown, the upper support arm, central joint, and lower support arm (or alternatively upper housing, central joint, and lower housing) can be integrally formed together as a single continuous static structure, wherein the resulting orthopedic brace functions as a splint having an adjustable length.

While the forgoing preferred embodiments of the invention have been described and shown, it is understood that alternatives and modifications, such as those suggested and others, may be made thereto and fall within the scope of the invention.

We claim:

1. An adjustable support assembly for an orthopedic brace comprising:
   a support arm;
   a housing including a travel track slidably receiving said support arm; and
   a locking mechanism including a lock lever and a pivot having a pivot axis aligned essentially perpendicular to a travel direction of said support arm in said travel track, wherein said lock lever is rotatable about said pivot axis in a rotation plane essentially parallel to said travel direction to selectively transition between a closed position and an open position, further wherein said lock lever applies a sufficient degree of a pressing force against said support arm in a force direction essentially perpendicular to said travel direction to prevent slidable displacement of said support arm in said travel track when said lock lever is rotated within said rotation plane about said pivot axis in a first direction to said closed position and said lock lever withdraws a sufficient degree of said pressing force from said support arm to enable slidable displacement of said support arm in said travel track when said lock lever is rotated within said rotation plane about said pivot axis in a second direction to said open position.

2. The adjustable support assembly of claim 1, wherein said lock lever has a head rotationally mounted on said housing at said pivot.

3. The adjustable support assembly of claim 2, wherein said locking mechanism further includes a lock chamber formed in said housing to receive said head, said lock chamber having an internal opening enabling access to said support arm in said travel track from said lock chamber.

4. The adjustable support assembly of claim 3 further comprising a friction plate positioned in said internal opening to engage said head and said support arm when said lock lever is in said closed position, wherein said lock lever applies said pressing force to said support arm via said friction plate.

5. The adjustable support assembly of claim 4, wherein said friction plate has a first layer engageable with said head and a second layer engageable with said support arm, further wherein said first layer is formed from a relatively non-compressible material and said second layer is formed from a relatively elastically compressible material.

6. The adjustable support assembly of claim 3, wherein said head engages said support arm through said internal opening to apply said pressing force to said support arm when said lock lever is in said closed position.

7. The adjustable support assembly of claim 1, further comprising a joint fixed to said support arm.

8. The adjustable support assembly of claim 7, wherein said joint is a rotational hinge.

9. The adjustable support assembly of claim 1 further comprising a joint fixed to said housing.

10. The adjustable support assembly of claim 9, wherein said joint is a rotational hinge.

11. An adjustable support assembly for an orthopedic brace comprising:
    a support arm;
    a housing including a travel track slidably receiving said support arm; and
    a locking mechanism including a lock lever, a lock chamber, and a friction plate, said lock lever having a head rotationally mounted on said housing, said lock chamber formed in said housing to receive said head and having an internal opening enabling access to said support arm in said travel track from said lock chamber, and said friction plate positioned in said internal opening engageable with said head and said support arm, wherein said lock lever is selectively transitionable between a closed position and an open position, further wherein said head applies a sufficient degree of a pressing force to said support arm via said friction plate to prevent slidable displacement of said support arm in said travel track when said lock lever is in said closed position and said head withdraws a sufficient degree of said pressing force from said support arm to enable slidable displacement of said support arm in said travel track when said lock lever is in said open position.

12. The adjustable support assembly of claim 11, wherein said friction plate has a first layer engageable with said head and a second layer engageable with said support arm, further wherein said first layer is formed from a relatively non-compressible material and said second layer is formed from a relatively elastically compressible material.

13. An orthopedic brace comprising:
    a first support assembly having a first support arm, a first housing including a first travel track slidably receiving said first support arm, and a first locking mechanism including a first lock lever and a first pivot having a first pivot axis aligned essentially perpendicular to a travel direction of said first support arm in said first travel track, wherein said first lock lever is rotatable about said first pivot axis in a rotation plane essentially parallel to said travel direction to selectively transition between a first closed position and a first open position, further wherein said first lock lever applies a sufficient degree of a first pressing force against said first support arm in a force direction essentially perpendicular to said travel direction to prevent slidable displacement of said first support arm in said first travel track when said first lock lever is rotated within said rotation plane about said first pivot axis to said first closed position and said first lock lever withdraws a sufficient degree of said first pressing force from said first support arm to enable slidable displacement of said first support arm in said first travel track when said first lock lever is rotated within said rotation plane about said first pivot axis to said first open position;

a second support assembly having a second support arm, a second housing including a second travel track slidably receiving said second support arm, and a second locking mechanism including a second lock lever and a second pivot having a second pivot axis aligned essentially perpendicular to a travel direction of said second support arm in said second travel track, wherein said second lock lever is rotatable about said second pivot axis in a rotation plane essentially parallel to said travel direction to selectively transition between a second closed position and a second open position, further wherein said second lock lever applies a sufficient degree of a second pressing force against said second support arm in a force direction essentially perpendicular to said travel direction to prevent slidable displacement of said second support arm in said second travel track when said second lock lever is rotated within said rotation plane about said second pivot axis to said second closed position and said second lock lever withdraws a sufficient degree of said second pressing force from said second support arm to enable slidable displacement of said second support arm in said second travel track when said second lock lever is rotated within said rotation plane about said second pivot axis to said second open position; and a joint connecting said first support assembly to said second support assembly.

14. The orthopedic brace of claim 13, wherein said joint is a rotational hinge.

15. The orthopedic brace of claim 13, wherein said joint is a static joint.

16. The orthopedic brace of claim 13, wherein said orthopedic brace is sized in correspondence with a leg of a user to enable mounting said orthopedic brace on said leg above and below a knee joint of said leg.

* * * * *